US00PP12877P2

(12) United States Plant Patent
Sorensen

(10) Patent No.: US PP12,877 P2
(45) Date of Patent: Aug. 27, 2002

(54) OSTEOSPERMUM PLANT NAMED 'BAMBA'

(76) Inventor: Carl Aksel Kragh Sorensen, Snapagervej 1, 8320 Aabyhoj (DK)

( * ) Notice: Subject to any disclaimer, the term of this patent is extended or adjusted under 35 U.S.C. 154(b) by 0 days.

(21) Appl. No.: 09/291,101

(22) Filed: Apr. 14, 1999

(51) Int. Cl.[7] ..... A01H 5/00

(52) U.S. Cl. ..... Plt./360

(58) Field of Search ..... Plt./360

(56) References Cited

PUBLICATIONS

UPOV CD–ROM, PBR 961164, Osteospermum designated Bamba, 1996.*

* cited by examiner

*Primary Examiner*—Bruce R. Campell
*Assistant Examiner*—June Hwu

(57) ABSTRACT

A distinct cultivar of Osteospermum plant named 'Bamba', characterized by its compact and uniform plant habit; ray florets that are initially lavender in color and darken to red purple with development; dark purple-tipped disc florets; and numerous inflorescences per plant.

1 Drawing Sheet

BACKGROUND OF THE INVENTION

The present invention relates to a new and distinct cultivar of Osteospermum plant, botanically known as *Osteospermum ecklonis* and referred to by the cultivar name Bamba.

The new cultivar is a product of a planned breeding program conducted by the Inventor in Aabyhoj, Denmark. The objective of the breeding program was to create new compact Osteospermum cultivars with interesting ray floret colors.

The new cultivar originated from a cross made by the Inventor in 1995 of a proprietary selection of *Osteospermum ecklonis* identified as 9512 as the female, or seed, parent and a proprietary selection of *Osteospermum ecklonis* identified as 9520 as the male, or pollen, parent. The new Osteospermum was selected by the Inventor as a flowering plant within the progeny of this cross in a controlled environment in Aabyhoj, Denmark, in 1996.

Plants of the new cultivar are different from plants of the female parent, the selection 9512, primarily in plant habit.

Plants of the new Osteospermum are different from plants of the male parent, the selection 9520, in plant size, number of ray florets and color of lower surface of ray florets.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Bamba'. These characteristics in combination distinguish 'Bamba' as a new and distinct cultivar:

1. Compact and uniform plant habit.

2. Ray florets that are initially lavender in color and darken to red purple with development.

3. Dark purple-tipped disc florets.

4. Numerous inflorescences per plant.

The new cultivar can be compared to the Osteospermum cultivar Cape Daisy Lusaka, disclosed in U.S. Plant Pat. No. 10,337. In side-by-side comparisons conducted in Aabyhoj, Denmark, and Encinitas, Calif., plants of the new cultivar are smaller, less vigorous and more uniform in plant habit; have smaller but more numerous inflorescences; have slightly shorter peduncles; and have a more saturated ray floret color than plants of the cultivar Lusaka.

The cultivar Bamba has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Bamba'.

The photograph at the bottom of the sheet is a close-up view of typical inflorescences and young and mature leaves of 'Bamba' (code number 9605 in the photograph) and 'Cape Daisy Lusaka' (Lusaka in the photograph). Foliage and floret colors in the photographs may appear different from the actual colors due to light reflectance.

DETAILED BOTANICAL DESCRIPTION

The following observations, measurements and values describe one-gallon containers of the new cultivar grown in Encinitas, Calif., under outdoor, full-sun conditions with day temperatures ranging from 20 to 27° C. and night temperatures ranging from 6 to 14° C. Plants were pinched (terminal apex removed) one time about two weeks after planting rooted cuttings. Plants used for this description were grown for about 12 to 14 weeks after planting rooted cuttings.

Color references are made to The Royal Horticultural Society Colour Chart except where general terms of ordinary dictionary significance are used.

Botanical classification: *Osteospermum ecklonis* cultivar Bamba.

Parentage:

*Female, or seed, parent.*—Proprietary selection of *Osteospermum ecklonis* identified as 9512.

*Male, or pollen, parent.*—Proprietary selection of *Osteospermum ecklonis* identified as 9520.

Propagation:

*Type.*—By terminal cuttings.

*Time to initiate roots.*—About 10 days at 18° C.

*Time to develop roots.*—About 21 days at 18° C.

*Rooting habit.*—Fibrous.

Plant description:

*Appearance.*—Perennial herbaceous container and garden plant. Inverted triangle. Very compact, upright and mounding growth habit. Freely branching with about 11 primary and about 10 secondary branches. Full plants with dense foliage and erect flower stems.

*Vigor.*—Moderate.

*Plant height.*—About 27 cm.

*Plant spread.*—About 53 cm.

*Lateral branch description.*—Length: About 8 to 12 cm. Diameter: Primary, about 7 mm; secondary, about 3 mm. Internode length: About 1 to 1.5 cm. Texture: Sparsely pubescent; woody at base. Color: 144A; upper surface tinged with 79A to 79B.

*Foliage description.*—Leaves alternate, single. Quantity of leaves per secondary branch: Numerous, about 26. Length, fully expanded leaves, basal: About 4.5 to 5.5 cm. Width, fully expanded leaves, basal: About 1.5 to 2 cm. Shape: Elliptic to lanceolate. Apex: Broadly acute. Base: Attenuate. Margin: Nearly entire with three to five widely-spaced teeth. Teeth typically present on older leaves. Aspect: Mostly flat. Texture: Smooth; thick and leathery; slightly pubescent on lower surface. Color: Young foliage, upper surface: 137A. Young foliage, lower surface: 137B. Fully expanded foliage, upper surface: 137A. Fully expanded foliage, lower surface: 137C. Attenuated leaf base: 137C to 137D. Venation, upper and lower surfaces: 137C.

Inflorescence description:

*Appearance.*—Daisy-type composite inflorescence form; actinomorphic. Single inflorescences displayed above foliage, upright on long peduncles arising from leaf axils. Disc and ray florets arranged acropetally on a capitulum. Typically about 92 opened and unopened inflorescences per plant. Inflorescences last about one week. Inflorescences persistent.

*Flowering response.*—Plants flower continuously from April to October in the Northern Hemisphere.

*Fragrance.*—None detected.

*Inflorescence size.*—Diameter: About 5 to 5.5 cm. Depth (height): About 2 to 2.5 cm. Diameter of disc: About 1 cm.

*Inflorescence buds.*—Length: About 1.6 cm. Width: About 8 mm. Shape: Ovoid. Color: 86A.

*Ray florets.*—Length: About 2.5 cm. Width: About 7 mm. Shape: Elliptical to ligulate. Apex: Tri-dentate, minute. Base: Acute. Margin: Entire. Texture: Smooth, satiny. Aspect: Upright to outward. Number of ray florets per inflorescence: About 18 to 20 in a single whorl. Color: When opening, upper surface: 75A to 75B. When opening, lower surface: Longitudinally striped, lavender, 76A, with yellowish green, 145B. Fully opened, upper surface: Longitudinally striped, red purple, 78A, with lighter red purple, 78B to 78C; base, 77A. Stripes less distinct and color more uniform, 78B, with subsequent development. Fully opened, lower surface: Longitudinally striped, purple, 77A, with lighter purple, 77B.

*Disc florets.*—Shape: Tubular; slightly salverform; five-lobed, fluted at apex. Number of disc florets per inflorescence: Numerous, about 76. Length: About 5 mm. Width: About 2 mm. Color: Immature: Apex, 97B; midsection, 76D. Mature: Apex, 86A; midsection, 76B.

*Phyllaries.*—Shape: Linear. Apex: Narrowly acute. Margin: Entire. Quantity and arrangement: About 18 per inflorescence; whorled. Texture: Coarse. Color: Upper surface: 137D. Lower surface: 137B.

*Peduncle.*—Length: About 7 cm. Aspect: Moderately strong to weak; inflorescences held above foliage. Texture: Hispid; coarse. Color: 147C.

*Reproductive organs.*—Androecium: Present on disc florets only. Stamens: Five. Anther shape: Oblong. Anther size: About 2 mm. Anther color: 86A. Pollen amount: Low. Pollen color: 23A. Gynoecium: Present on ray and disc florets. Pistils: One. Pistil length: About 5 mm. Stigma shape: Bipartate. Stigma color: 86A. Style length: About 3 mm. Style color: 86A to 86B. Ovary color: 142D.

*Seed, immature.*—Length: About 4 mm. Diameter: About 2 mm. Color: Green.

Disease resistance: Resistance to pathogens common to Osteospermum has not been observed.

It is claimed:

1. A new and distinct cultivar of Osteospermum plant named 'Bamba', as illustrated and described.

* * * * *

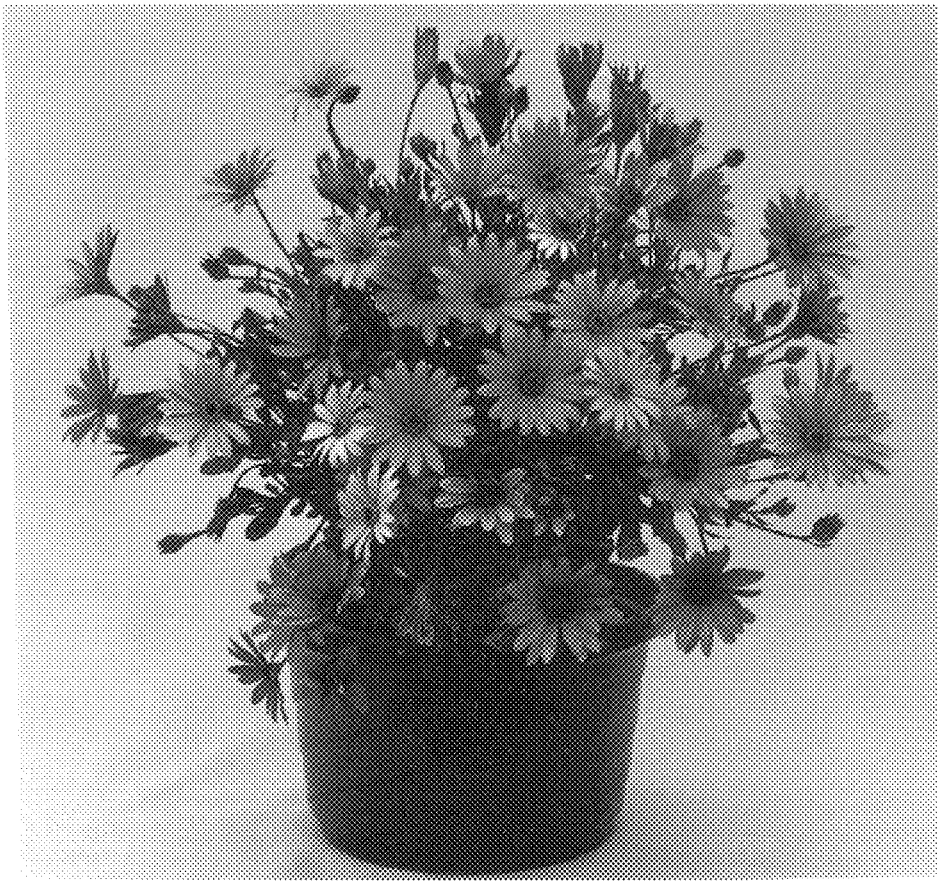
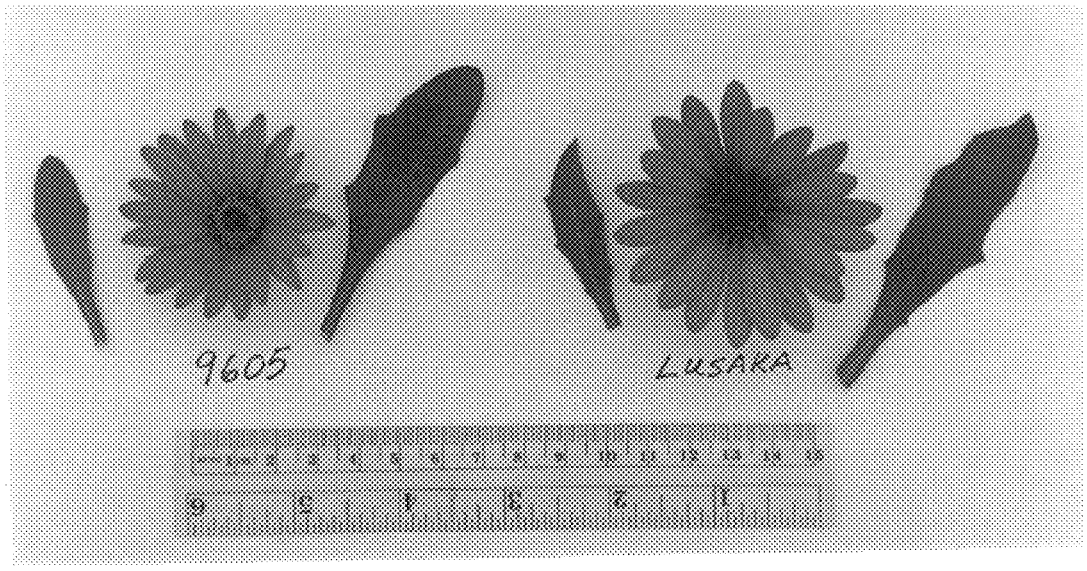
9605
LUSAKA